(12) United States Patent
Azanza Ladrón et al.

(10) Patent No.: US 10,267,836 B2
(45) Date of Patent: Apr. 23, 2019

(54) QUALITY INSPECTION OF THIN FILM MATERIALS

(71) Applicants: DAS-NANO, S.L., Tajonar (ES); ASOCIACION CENTRO DE INVESTIGACIÓN COOPERATIVA EN NANOCIENCIAS (CIC NANOGUNE), Donostia (ES); GRAPHENEA, S.A., Donostia (ES)

(72) Inventors: Eduardo Azanza Ladrón, Gorraiz (ES); Magdalena Chudzik, Mutilva Baja (ES); Alex López Zorzano, Mutilva Baja (ES); David Etayo Salinas, Mutilva Baja (ES); Luis Eduardo Hueso Arroyo, Donostia (ES); Amaia Zurutuza Elorza, Donostia (ES)

(73) Assignees: DAS-NANO, S.L., Tajonar (ES); ASOCIACION CENTRO DE INVESTIGACION COOPERATIVE EN NANOCIENCIAS (CIC NANOGUNE), Donostia (ES); GRAPHENEA, S.A., Donostia (ES)

( * ) Notice: Subject to any disclaimer, the term of this patent is extended or adjusted under 35 U.S.C. 154(b) by 0 days.

(21) Appl. No.: 15/539,091

(22) PCT Filed: Dec. 23, 2014

(86) PCT No.: PCT/EP2014/079171
§ 371 (c)(1),
(2) Date: Jun. 22, 2017

(87) PCT Pub. No.: WO2016/102003
PCT Pub. Date: Jun. 30, 2016

(65) Prior Publication Data
US 2018/0164354 A1    Jun. 14, 2018

(51) Int. Cl.
  *G01R 27/02*    (2006.01)
  *G01N 21/3581*    (2014.01)
  *G01N 21/84*    (2006.01)
  *G01N 21/17*    (2006.01)

(52) U.S. Cl.
  CPC ......... *G01R 27/02* (2013.01); *G01N 21/3581* (2013.01); *G01N 21/84* (2013.01); *G01N 21/8422* (2013.01); *G01N 2021/178* (2013.01)

(58) Field of Classification Search
  CPC ... G01R 27/02; G01N 21/84; G01N 2021/178
  See application file for complete search history.

(56) References Cited

U.S. PATENT DOCUMENTS 9,372,215 B2    6/2016    Hamano
2001/0029436 A1*    10/2001    Fukasawa .......... G01N 21/3581
                                                          702/117

(Continued)

FOREIGN PATENT DOCUMENTS

EP    2642277 A1    9/2013
WO    WO 2011/108462 A1    9/2011

OTHER PUBLICATIONS

International Search Report and Written Opinion of the International Searching Authority dated Sep. 22, 2015 for PCT/EP2014/079171, 12 pages.

(Continued)

*Primary Examiner* — Marcus H Taningco
(74) *Attorney, Agent, or Firm* — Squire Patton Boggs (US) LLP (57) ABSTRACT

Devices and methods for determining the quality thin film materials are disclosed. The thin film materials are provided on substrates forming thin film material structures. The devices comprise a housing, a THz module with a THz source emitter and a THz detector, and a reflective base moveable relative to the THz module and configured to (Continued)

support the thin film material structures. The THz source emitter is configured to irradiate the thin film materials. The THz detector is configured to measure at least one reflection of the irradiation. The device is configured to calculate a parameter indicative of the quality of the thin film material based on said reflection measurements.

14 Claims, 11 Drawing Sheets

(56) References Cited

U.S. PATENT DOCUMENTS

| | | | |
|---|---|---|---|
| 2011/0058155 A1* | 3/2011 | Ohno | G01N 21/3581 356/51 |
| 2013/0249573 A1* | 9/2013 | Hamano | G01N 21/3581 324/702 |
| 2018/0038814 A1* | 2/2018 | Kim | G01N 27/04 |

OTHER PUBLICATIONS

Buron, Jonas D., et al., "Graphene Conductance Uniformity Mapping," Nano Letters 2012, vol. 12, pp. 5074-5081.

Liang, Min, et al., "Terahertz characterizartion of Single-Walled Carbon Nanotube and Graphene On-Substrate Thin Films," IEEE Transactions on Microwave Theory and Techniques, Oct. 1, 2011, vol. 59, No. 10, pp. 2719-2725.

Rouhi, Nima, et al., "Terahertz Graphene Optics," Nano Research, Oct. 2012, vol. 5, Issue 10, pp. 667-678.

\* cited by examiner

QUALITY INSPECTION OF THIN FILM MATERIALS

The present disclosure relates to thin film materials and more specifically to devices and methods for evaluating the quality of thin film materials by measuring their conductivity.

BACKGROUND ART

Thin film materials made of thin sheets of atoms are novel structures characterized by unique specifications that can be used to improve electrical, mechanical, thermal, and optical properties of other materials. Graphene is an example of such atomically thin materials with many commercial applications, either proposed and/or under development in a variety of technical areas. The behavior of transmitted and reflected electromagnetic waves when they interact with thin film materials depends on several properties, most importantly, on their sheet conductivity, in such a way that areas of higher sheet conductivity are characterized by higher reflectivity and areas of higher transmittance are related with lower sheet conductivity of this material. The conductivity of the material and, thus, transmission and reflection coefficients are frequency dependent parameters and they can be measured in a wide range of the frequency spectrum, including ultra-violet range, visible range, infrared range, terahertz range, millimeter-waves and microwaves. The sheet conductivity of the thin-film is related to the average transport properties (such as the carrier density and mobility) of the material and can be used to characterize its electrical continuity and uniformity. The small-scale and large-scale measurement of the conductivity is an important issue in the non-contact quality inspection of thin film materials.

Several methods exist to inspect the quality of thin films, in some cases by measuring the conductivity of this material. One typical method used is the micro four-point probe, also known as the Van der Pauw technique. This measurement technique is characterized by its low reliability and spatial resolution as it provides a single value of DC conductivity of the whole sample (see "*Graphene Conductance Uniformity Mapping*", Buron et al., Nanoletters, 12 (10), pp 5074-50812012). In addition, this characterization method belongs to the group of invasive characterization methods, as some metallic contacts are required to perform the measurements. Another method used is confocal Raman spectroscopy. It should be noted that confocal Raman Spectroscopy is only used for active Raman materials. This technique provides information about the defects, doping density, mechanical strain, and the number of thin film layers in the sample by performing micro-scale measurements. It is important to remark that confocal Raman spectroscopy is characterized by low throughput as the acquisition time is limited by the low efficiency of Raman scattering and the size of the single point is restricted to the spot size of the laser used (around 500 nm). Thus, in order to characterize the material, the time-consuming raster scan needs to be performed across the entire sample. Consequently, Raman spectroscopy is not an adequate method to characterize large-scale samples ($\geq 10$ cm$^2$). A third method is optical imaging. The optical imaging merely provides quality information about the full area of the sample. Moreover, it does not provide any quantitative information about the distribution of the conductivity in the sample. Another method used for the characterization of thin materials is the use of an Atomic Force Microscope (AFM). It can provide a topological map of the surface of the sample but it requires several hours to map a single sample with an area of 1 cm$^2$. Moreover, the usage of this measurement technique may lead in some cases to damages in the material under test. Finally, Transmission Electron Microscopy (TEM) is also used to get the information about the quality of thin film materials. For instance, in order to analyse the graphene, it has to be transferred onto 3 mm TEM grids. This technique provides a lot of information about the graphene material such as grain size, grain boundary structure, number of graphene layers, etc. however it is a destructive technique and only small areas can be investigated Due to the rapid growth of the thin film material market and the necessity of obtaining thin film materials of larger areas, brand new methods are required in order to provide fast and reliable techniques to characterize the quality of the fabricated materials both inside and out of the production line. Thus, the conductivity of thin materials can be used as one of the parameters to assess the uniformity of the material. Moreover, this system may be used to test the reproducibility and repeatability of the fabrication process for small (<10 cm$^2$) or large-area ($\geq 10$ cm$^2$) thin film materials (see "*Terahertz Graphene Optics*", Rouhi et al., Nano Res, October 2012, Volume 5, Issue 10, pp 667-678).

Several examples included in the literature present the methods to calculate the conductivity of thin film materials using the transmission configuration, which is often not appropriate in an industrial process as it requires placing the radiation emitter and detector at the opposite sides of the measured material. Thus, a technique that allows a more practical implementation of this type of inspection is very desirable.

SUMMARY OF THE INVENTION

The quality of the thin film materials may be assessed by analysing the uniformity of the conductivity in the material. The conductivity is obtained by measuring changes in the reflectivity and transmittance of the thin film material. In the case of thin film materials, e.g. graphene, comprising single or multi-layer form, the precise value of the conductivity may be obtained. In the case of other forms of thin film materials, e.g. graphene powders, flakes, ribbons, the distribution of these dopants in the used matrix may be obtained by detecting changes in conductivity between the selected zones of the bulk sample. Both pulsed and continuous wave (CW) THz systems may be suitable for the analysis of the conductivity of the sample. In the case when a CW THz system is used, both the amplitude and phase of the reflected signal need to be provided in order to obtain the equivalent time-domain signal.

In a first aspect, a device to determine the quality of a thin film material is disclosed. The thin film material is provided on a substrate where they form a thin film material structure. The device comprises a housing, a THz module and a reflective base. The THz module comprises a THz source emitter and a THz detector. The reflective base is moveable relative to the THz module and configured to support the thin film material structure. Either the THz module, or the reflective base or both may be moveable. Upon irradiation of the thin film material with the THz source emitter, the THz detector is configured to measure at least one reflection of the irradiation and the device is configured to calculate a parameter indicative of the quality of the thin film material in response to said at least one reflection measurement. Both the THz source emitter and the THz detector are located at the same side of the thin film material structure.

The thin film can be considered as a substantially zero-thickness material. Therefore, any reflection from the thin film material, i.e. from the air-film interface, and any reflection from the substrate, i.e. from the interface between the thin film and the substrate may be considered as the same reflection. The at least one reflection may be the air-film-substrate reflection or the reflection from the substrate-base interface, i.e. the interface between the substrate and the base, or from both.

The substrate may comprise a single layer substrate or a multi-layer substrate forming a stacked substrate. When a multi-layer substrate is used, each layer may comprise the same material or different materials. Each interface between layers of the stacked substrate may provide a reflection to be measured. In some examples, a layer of the multi-layer substrate may be reflective enough that the reflection from this layer's interface may act as the reflection from the base. Effectively, this layer and all the layers below this reflective layer may be considered to form part of the reflective base.

In some examples, to determine the quality of thin film materials, the reflection which contains information from the air-film-substrate interface and/or the reflection which contains information from the substrate-reflective base interface are measured when the thin-film material has already been deposited on the substrate. Moreover, in some examples, a reference measurement is required, where the reflection which contains information from the air-substrate interface and/or the reflection which contains information from the substrate-reflective base interface are measured when the bare substrate is analysed. Furthermore, in other examples, the THz signal may be manipulated using any kind of analog or digital processing techniques including the reflection may be filtered, gated, de-convoluted, fitted by a polynomial or transformed into a different domain (i.e. by a Fourier Transform, Laplace transform or Z-transform).

In some examples, the quality of the thin film material can be determined by the conductivity which is calculated using the relative transmission coefficient calculated from the reflections of the irradiation from the substrate-reflective base interface obtained from measurements performed in the case when the thin-film material is deposited and in the case when the bare substrate is analysed. In other examples, the quality may be determined by other parameters, such as reflection coefficient, reflected power, time delay between reflected pulses, refractive index or permittivity. This list of parameters is provided only as an example. Other parameters indicative of the quality of the material may also be calculated using the method and devices disclosed herein.

In some examples, the conductivity may be determined at a single point of the thin-film samples. In other examples, raster scanning may be performed in order to calculate the conductivity at the adjacent points of the thin-film sample in order to obtain a large-area map of THz conductivity within the entire thin film material sample. The large-area map of THz conductivity, in turn, provides a quality metric where the effect of several physical features of the material, such as defects (e.g holes or multilayer points) and variations in doping density, is reflected. Additionally or alternatively other parameters may be calculated to create the map and assess the quality of the material.

The present invention demonstrates an advantage compared to other solutions for obtaining the THz conductivity of the material disclosed in the literature where the transmission configuration is used and, thus, the access to the bottom side of the sample is required. The solution given in the present invention is based on the measurement using a reflection configuration and thus allows the positioning of both the THz source emitter and the THz detector at the same side of the sample under test. This aspect of the invention is fundamental for its practical application in industry as a quality inspection tool.

Another advantage of using the THz radiation for quality inspection of the thin film material is the fact that it is a non-contact method and, thus, it does not require ohmic contacts, which may affect measurement results and lead to damages in the surface of the sample. At the same time, it bridges the gap between nano/micro scale tools and macro, whole-sample scale tools. Therefore, the method is less time-consuming and it offers an efficient alternative for the electrical characterization of small-scale and large-scale samples of thin film materials. Note that, the term of small-scale refers to the samples that have the area of less than 10 $cm^2$, while the large-scale sample has an area of at least 10 $cm^2$ or larger. In some embodiment, large-scale samples are linked together to create structures that include multiple large-scale samples.

In some examples, the THz source emitter and the THz detector are incorporated in a single THz source/detector module and wherein the irradiation and reflection directions coincide. This allows for a compact design of the device and easier alignment of the thin film material structure.

In some examples, several THz sources/detectors modules or an array of THz modules may be used in order to improve the speed of the measuring system.

In other examples, the THz source emitter and the THz detector are spaced apart and wherein the incidence of the irradiation is oblique with an angle of incidence $\alpha$. This allows for the easier separation of the emitted and received signal thus avoiding interferences.

In example applications, the thin film material may comprise an atomically thin material, for example, graphene in the form of a mono-layer graphene sample or a multi-layer graphene sample. In other example applications, the thin film material may comprise a transition metal dichalcogenide. In other example applications, the thin film material may comprise a transition metal oxide such as an insulating hexagonal boron nitride (BN), bismuth telluride (Bi2Te3), bismuth selenide (Bi2Se3), ZnCuS. In other example applications, the thin film material may comprise other materials that may be deposited or grown on substrates, such as Indium Tin Oxide (ITO), Poly(3,4-ethylenedioxythiophene) (PEDOT), TiO2 or Indium Gallium Zinc Oxide (IGZO), Niobium Carbide (NbC), GaAs/GaAlAs heterostructures conductive interfaces such as STO/LAO or oxide conductive thin film, such as superconductive La2CuO4 and magnetic LCMO. ITO is a material typically used in liquid crystal displays, flat panel displays, plasma displays, touch panels, and electronic ink applications. An ITO layer is used in the production of this kind of devices and it is transparent at the THz frequency range. However, such devices include a ground plane above which the ITO layer is deposited. This ground plane may be used as the reflective base for quality inspection of the ITO layer on these devices.

In other examples, the thin film material may comprise a material doped with alternative forms of graphene, such as graphene powders, flakes, or ribbons. In other examples, the thin film material may comprise an encapsulated thin film or an externally doped thin film. This list of materials is provided only for illustration and does not restrict in any way the scope of the invention to the materials described therein.

In some examples, the reflective base may be made of metal or doped semiconductor. In other examples, any type of material may be used, provided that it demonstrates high reflectivity (above 50%) in the THz frequency range.

In some examples, the device may further comprise a control panel with a display and control elements, such as switches. Therefore, the measurements and the results may be demonstrated in the same apparatus. This may allow for off-line inspection of the materials for research and small-scale quality control applications.

In some examples, the THz module may be housed in the housing and the reflective base may be movable relative to the housing. Maintaining the housing position fixed and moving the conductive base allows for precise measurements to be taken as the point of reference of the measurements remains steady.

In some examples, the device may further comprise an XYZ linear actuator and/or RX, RY, RZ roll actuator, configured to selectively move and/or roll the reflective base to change the distance and/or the angle between the THz source emitter and the surface of the thin film material as well as the point of incidence of the irradiation. Using an XYZ linear actuator and/or RX, RY, RZ roll actuator allows for moving and/or rolling the base and the sample with precision relative to the THz module.

In some examples, the reflective base may be housed in the housing and the THz module may be moveable relative to the housing. This may be beneficial in some applications, e.g. when the material to be measured is very delicate and any movement may disrupt its properties.

In some examples, the device may further comprise an XYZ linear actuator and/or RX, RY, RZ roll actuator, configured to selectively move and/or roll the THz module to change the distance (angle) between the THz source emitter and the surface of the thin film material as well as the point of incidence of the irradiation. The XYZ linear actuator and/or the RX, RY, RZ roll actuator may reduce any vibrations during the movement of the THz module, thus allowing a faster measurement process.

In some examples, the device may further comprise a processing module to calculate the conductivity of the thin film material based on said reflection measurements. This may allow local processing of the measurements and direct results. Alternatively or additionally, the device may further comprise a communication module to transmit said first and/or second reflection measurements to a remote processing module. The remote processing module may process the measurements and/or transmit back the results for display and/or store them for future or statistical use.

In some examples, the device may be integrated in a production line of the thin film material and configured to inspect said thin film material during its production. The production line may comprise a single or several THz modules and a reflective base. The THz module may comprise a THz source emitter and a THz detector. The reflective base may be placed below the sheet of the thin-film material obtained by, e.g., a roll-to-roll process. This allows for quick assessment and classification of the produced material as well as immediate detection of any abnormalities during the production phase. In some examples, such as graphene production, the differences in the quality of the material could be produced by changes in the temperature, pressure, gas flux and/or deposition time. These factors are mere examples and do not restrict in any way the scope of the invention.

In some examples, the THz source emitter is configured to operate within the range of 0.1 THz to 30 THz. Electromagnetic radiation from the terahertz (THz) band defined in the frequency range from 0.1 THz to 30 THz is non-ionizing radiation and has the favourable properties of high resolution (under 1 mm) and good transmission in dielectric materials (e.g. a sample of 1 mm thick quartz has a transmittance higher than 75%), which results in obtaining high contrast between conductive and dielectric materials. Therefore, electromagnetic waves from the THz range may be used for the characterization of one-dimensional and two-dimensional structures, such as graphene.

By analysing results provided in the aforementioned THz frequency range, changes in the conductivity of the thin materials, such as graphene, can be detected. Any contrast in conductivity between areas of the sample may be caused by an increment of defects in the sample (in the case of a decline of conductivity), by an inhomogeneity in the doping or by changes in the thickness of a deposited layered structure or by other factors related to the growth conditions. Thus, the results of the proposed method may indicate the quality factor of the sample under test. Moreover, in case the material is provided in layers, they may be used to determine the number of layers of the material sheets.

For instance, the proposed measurement procedure can be detailed for the case of a graphene sample.

Figure 1A:
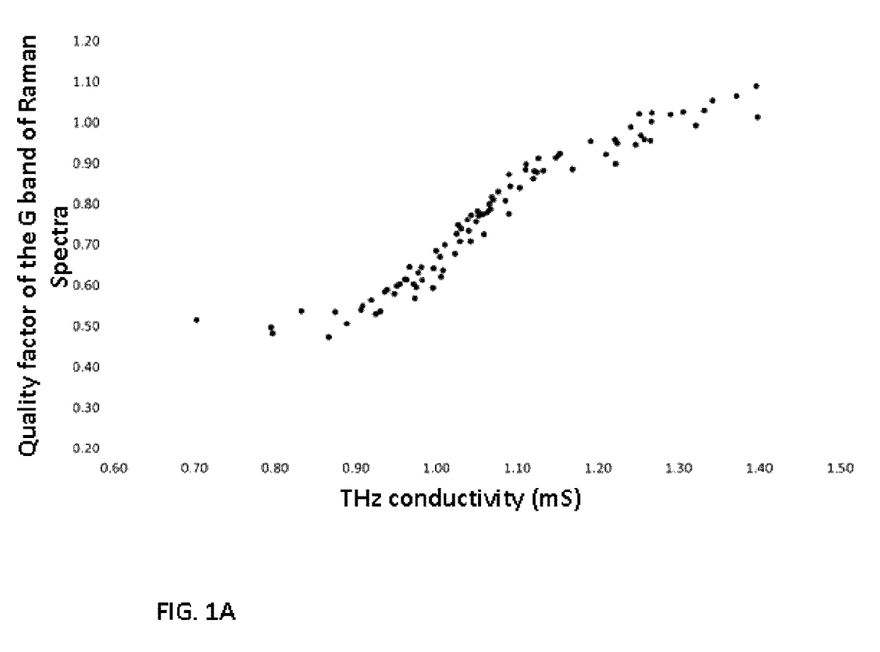
FIG. 1A is a graph illustrating the correlation between Raman spectroscopy and THz inspection.

Compared to other inspection methods, the THz inspection provides a number of benefits. Compared to the 4-Probe Method, THz inspection is a non-invasive technique and it allows obtaining maps of THz quality within the entire sample. Compared to confocal Raman spectroscopy, THz inspection provides information about the quality of the thin film material within the selected area of the sample and allows studying the homogeneity of the conductivity of the sample with a much shorter measuring time (For example, for an area of 1 mm$^2$, the THz method disclosed herein is at least 20 times faster than confocal Raman Spectroscopy). As the confocal Raman Spectroscopy is the most used technique for thin film characterization, it is important to demonstrate the correlation between Raman measurements and THz inspection. In order to validate it, several measurements using THz inspection and confocal Raman spectroscopy have been done and a correlation between the conductivity obtained by THz inspection and the Raman parameters has been obtained. FIG. 1A is a graph illustrating the correlation between Raman spectroscopy (defects) and THz inspection (conductivity). As shown in FIG. 1A, THz measurements present a good correlation (>80%) with measurements of confocal Raman spectroscopy. More specifically, the conductivity measurements with THz irradiation correlate with the quality factor of the G band of Raman Spectroscopy. Now, compared to optical Microscopy, THz inspection provides quantitative information about the sample by the characterization of the distribution of the conductivity. Compared to AFM THz inspection is a non-destructive method, which can provide a tomography map of the surface, with less resolution, and consuming much less time (For an area of 1 mm$^2$ THz is more than 100 times faster than AFM). Finally, compare with TEM, THz inspection provides a lower-resolution scale (THz inspection has a resolution down to 0.1 mm and TEM resolution is in nano-scale) consuming much less time (For an area of 1 mm$^2$ THz is more than 100 times faster than TEM).

In another aspect, a method of determining the conductivity of a thin film material using reflection measurements is disclosed. The thin film material may be provided on a substrate forming a thin film material structure. The method comprises providing the thin film material structure on a reflective base of a device according to aspects disclosed herein; irradiating the thin film material structure with the THz source emitter of the device; measuring at least one reflection of the irradiation and calculating a parameter indicative of the quality of the thin film material in response to said at least one reflection measurement.

In some examples, the method may further comprise measuring said at least one reflection for a range of frequencies at a plurality of points of the thin film material; calculating the parameter indicative of the quality of the thin film material at said plurality of points; generating a quality map of the thin film material.

In all examples disclosed herein, the thin film material may additionally be exposed to the influence of external forces, processes, and electromagnetic radiation, which may modify physical or chemical properties of the thin film material or the substrate, on which the thin film material is formed, in order to enhance the characteristics of the thin film material or the substrate to facilitate the calculation of thin film conductivity in the terahertz range. These external factors are applied in order to increase the contribution of the reflectivity of the thin film material over the reflectivity of the substrate. The external factors may be one of the following examples or a combination thereof:

External illumination of the thin film material and/or the substrate, on which the thin film material is formed, with electromagnetic radiation from the optical spectrum. The optical spectrum may include the ultra-violet (UV) range, the visible range, and/or the infrared (IR) range. The electromagnetic radiation from the optical spectrum may be coherent or non-coherent. The external illumination in the optical spectrum applied may be obtained from the continuous-wave (CW) or pulsed radiation sources.

Exposure of the thin film material and/or the substrate, on which the thin film material is formed, to external electromagnetic radiation from the high-energy part of the spectrum, such as x-rays and gamma rays.

External magnetic field applied to the thin film material and/or the substrate, on which the thin film material is formed, which may produce a Lorentz force acting on a charged particles moving with instantaneous velocity. The external magnetic field may be continuous or alternating, uniform or non-uniform.

External electric field applied to the thin film material and/or the substrate, on which the thin film material is formed, in order to concentrate free charge carriers (positive or negative charge) in selected areas of the thin film material and/or selected areas of the substrate to enhance the response of the thin film material and/or the substrate. The external electric field may be continuous or alternating, uniform or non-uniform.

External current driven across the thin film material and/or the substrate, on which the thin film material is formed, in order to concentrate free charge carriers (positive or negative charge) in selected areas of the thin film material and/or selected areas of the substrate to enhance the response of the thin film material and/or the substrate. The external current may be direct or alternating.

External voltage applied to bias the thin film material and/or the substrate, on which the thin film material is formed, in order to concentrate free charge carriers (positive or negative charge) in selected areas of the thin film material and/or selected areas of the substrate to enhance the response of the thin film material and/or the substrate. The external voltage applied may be direct or alternating.

The change in the distribution of the free charge carriers follows Maxwell's equations and it is applied to enhance the response of the thin film structure (changes in the free charge carrier distribution generate changes in the conductivity of the thin film structure). The external electric field, the voltage source and the current source may be continuous or alternating, uniform or non-uniform.

Other external factors that may be applied are:

External surface acoustic wave applied to the thin film material and/or the substrate, on which the thin film material is formed, introducing local disturbance of the mechanical properties of the thin film material and/or the substrate.

External mechanical strength applied to the thin film material and/or the substrate, on which the thin film material is formed introducing surface compression-tension strain in the thin film material and/or the substrate.

External heating or cooling applied to the thin film material and/or the substrate, on which the thin film material is formed.

Chemical processes and reactions applied to the thin film material and/or the substrate, on which the thin film material is formed.

In another aspect, a computing device is disclosed. The computing device may comprise a memory and a processor. The memory may store computer program instructions executable by the processor. Said instructions may comprise functionality to execute a method of inspecting a thin film material according to examples disclosed herein.

In yet another aspect, a computer program product is disclosed. The computer program product may comprise instructions to provoke that a computing device implements a method of inspecting a thin film material according to examples disclosed herein.

The computer program product may be embodied on a storage medium (for example, a CD-ROM, a DVD, a USB drive, on a computer memory or on a read-only memory) or carried on a carrier signal (for example, on an electrical or optical carrier signal).

The computer program may be in the form of source code, object code, a code intermediate source and object code such as in partially compiled form, or in any other form suitable for use in the implementation of the processes. The carrier may be any entity or device capable of carrying the computer program.

For example, the carrier may comprise a storage medium, such as a ROM, for example a CD ROM or a semiconductor ROM, or a magnetic recording medium, for example a hard disk. Further, the carrier may be a transmissible carrier such as an electrical or optical signal, which may be conveyed via electrical or optical cable or by radio or other means.

When the computer program is embodied in a signal that may be conveyed directly by a cable or other device or means, the carrier may be constituted by such cable or other device or means.

Alternatively, the carrier may be an integrated circuit in which the computer program is embedded, the integrated circuit being adapted for performing, or for use in the performance of, the relevant methods.

BRIEF DESCRIPTION OF THE DRAWINGS

Particular examples of the present invention will be described in the following by way of non-limiting examples, with reference to the appended drawings, in which.

DETAILED DESCRIPTION OF EXAMPLES

Figure 1B:
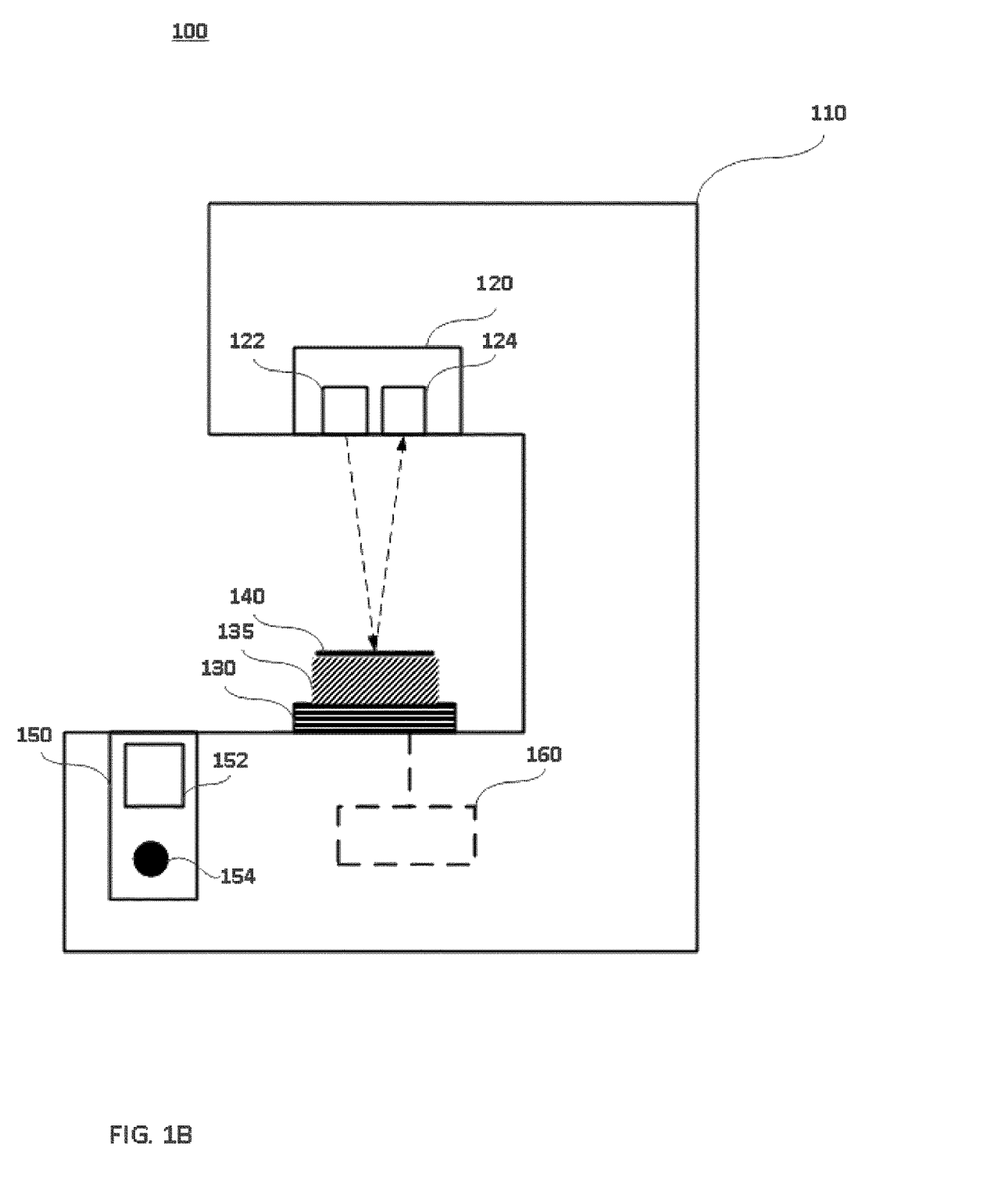
FIG. 1B illustrates a device to inspect a thin film material according to an example.

FIG. 1B illustrates a device to determine the quality of a thin film material according to an example. Device 100 may comprise a housing 110, a THz module 120 and a reflective base 130. The THz module 120 may comprise a THz source emitter 122 and a THz detector 124. A thin film material 140 is illustrated on top of a substrate 135. An actuator 160 may selectively move the reflective base 130 to change the distance between the THz source emitter 122 and the surface of the thin film material 140 as well as the point of incidence of the irradiation.

During a sample inspection process, the sample 140 to be measured is placed on the reflective base 130, to maximize the reflection of the signal. The reflective base 130 may be a metallic base. However, other materials with a high conductivity, i.e. materials with high reflectivity in the THz frequency range, such as semiconductor materials (e.g. doped silicon or similar) may be used as materials for the reflective base 130. Now, the actuator 160 may be an XYZ linear actuator and/or an RX, RY, RZ roll actuator configured to move and/or roll the reflective base 130 and any sample placed thereupon in three dimensions. For example the actuator 160 may be a linear stage XYZ actuator (or 6 axis actuator for complex thin film materials). Using the actuator 160 the sample 140 may be moved in the Z direction, to adjust the distance between the source emitter 122 and the sample 140 in order to focus the signal on the surface of the reflective base 130. The focal length may be given by the parameters of the optical components utilized in the system. The distance in the Z direction may be adjusted manually or utilizing a motorized stage with the aim of maximizing the signal reflected from the interface between the substrate and the reflective base.

Initially, a reference measurement may be performed using the bare substrate 135 to obtain a signal which contains information from the interface between the bare substrate 135 and the reflective base 130. Analyzing the obtained signal, a temporal window may be applied in order to separate the part of the signal related with the above-mentioned interface and the Fourier transform may be used to calculate its spectrum Secondly, the substrate 135 with a thin film material 140 may be introduced and an analogous measurement may be performed. As a result the spectrum of the signal related with the interface between the substrate 135 and the reflective base is obtained, which contains the information about the transmission properties of the substrate 135 and the thin film 140.

Figure 1C:
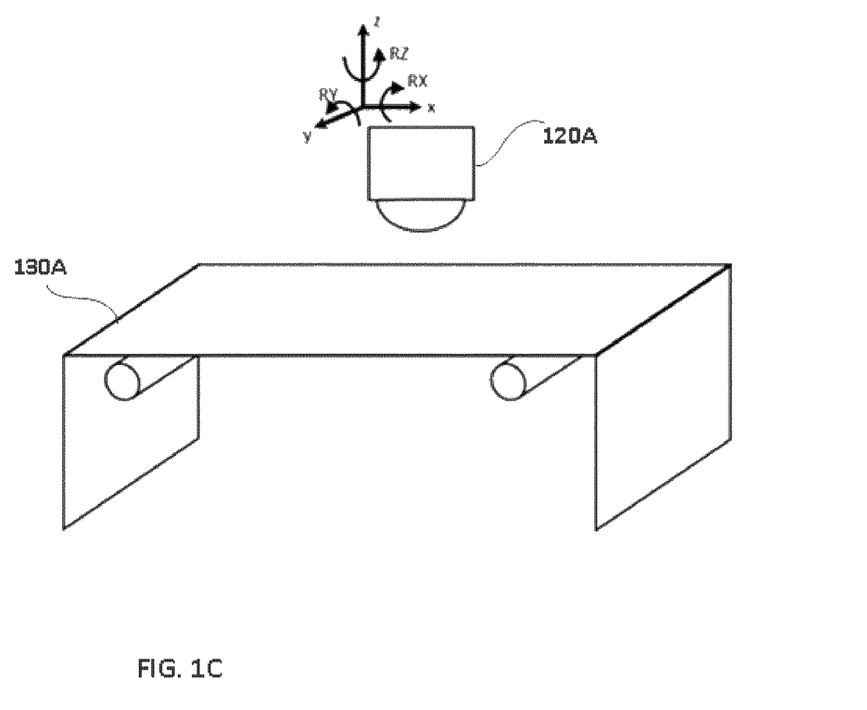
FIG. 1C illustrates an example device for making on-line THz inspection of materials.

FIG. 1C illustrates an example stand-alone device for making on-line THz inspection of materials. The device comprises a THz module 120A or an array of THz modules, and a roll-to-roll reflective base 130A, on where thin film structures may be analysed. The roll-to-roll reflective base, and along with it any thin film structure on top of it, may be moveable along a first direction x, while the THz module may be moveable in any direction xyz. Therefore, any point of the thin film structure may be measured during a production process.

Figure 1D:
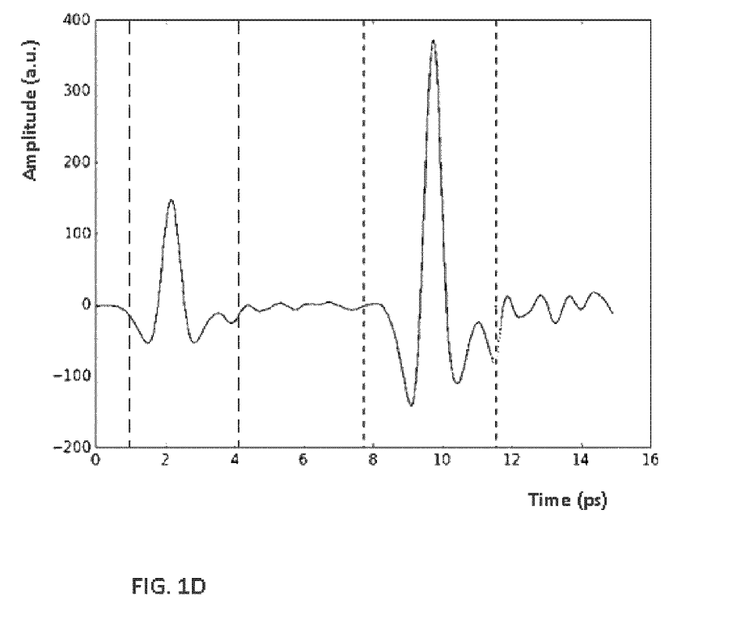
FIG. 1D illustrates example temporal windows of a THz signal reflection measurement when the thin film is deposited on the substrate.

FIG. 1D illustrates an example graph with temporal windows of a THz signal reflection measurement when the thin film is deposited on the substrate. In this graph the amplitude of the reflected signal over the structure film-substrate is represented. During a first time period, the reflection from the air-film-substrate interface is received. Then, during a second time period the reflection from the interface substrate-base is received. Similar graph characteristics may be generated when the bare substrate is measured.

Using the reference measurement and the result for the sample with the thin film sample, the relative reflectance which depends on the transmission through the thin film layer can be calculated for the thin film sample using the following expressions:

$$R_{air\text{-}substrate} = t_{13}^2 \cdot \frac{1}{1 - r_{31}} \quad \text{Eq. 1}$$

$$R_{air\text{-}film\text{-}substrate} = t^2 \cdot \frac{1}{1 - r} \quad \text{Eq. 2}$$

where $R_{air\text{-}substrate}$ is the total reflectance of the bare substrate sample, when the reflection which contains information from the substrate-base interface is considered, and $R_{air\text{-}film\text{-}substrate}$ is the total reflectance of the sample, when the thin film is deposited on the substrate and the reflection which contains information from the substrate-base interface is considered.

As presented in the equations 1 and 2, $t_{13}$ is the transmission Fresnel coefficient through the air-substrate interface, $r_{31}$ is the reflection Fresnel coefficient from the substrate-air interface, t is the transmission Fresnel coefficient through the air-film-substrate interface, r is the reflection Fresnel coefficient from the substrate-film-air interface and they are defined as:

$$t_{13} = \frac{2 \cdot n_1}{n_1 + n_3} \quad \text{Eq. 3}$$

$$r_{31} = \frac{n_3 - n_1}{n_3 + n_1} \quad \text{Eq. 4}$$

$$t = \frac{2}{n_3 + 1 + Z_0 \cdot \sigma} \quad \text{Eq. 5}$$

$$r = \frac{n_3 - 1 - Z_0 \cdot \sigma}{n_3 + 1 + Z_0 \cdot \sigma} \quad \text{Eq. 6}$$

where $n_1$ is the refractive index of air, $n_3$ is the refractive index of the substrate, $Z_0$ is the vacuum impedance, and $\sigma$ is the sheet conductivity of the thin film layer.

Thus, the relative reflectance $R_{rel}$ is given by:

$$R_{rel} = \frac{R_{air\text{-}film\text{-}substrate}}{R_{air\text{-}substrate}} = \left|\frac{t^2}{t_{13}^2}\right|^2 \cdot \frac{1-|r_{31}|^2}{1-|r|^2} \quad \text{Eq. 7}$$

Knowing the relative transmission of the thin film, the sheet conductivity can be calculated at that point of the sample.

Using the actuator 160 to move the conductive base 130 in the XYZ direction, the sample 140 is moved with respect to the emitting source 122 and the same measurement procedure and calculation of the THz sheet conductivity is repeated in the next point of the sample 140.

Figure 1E:
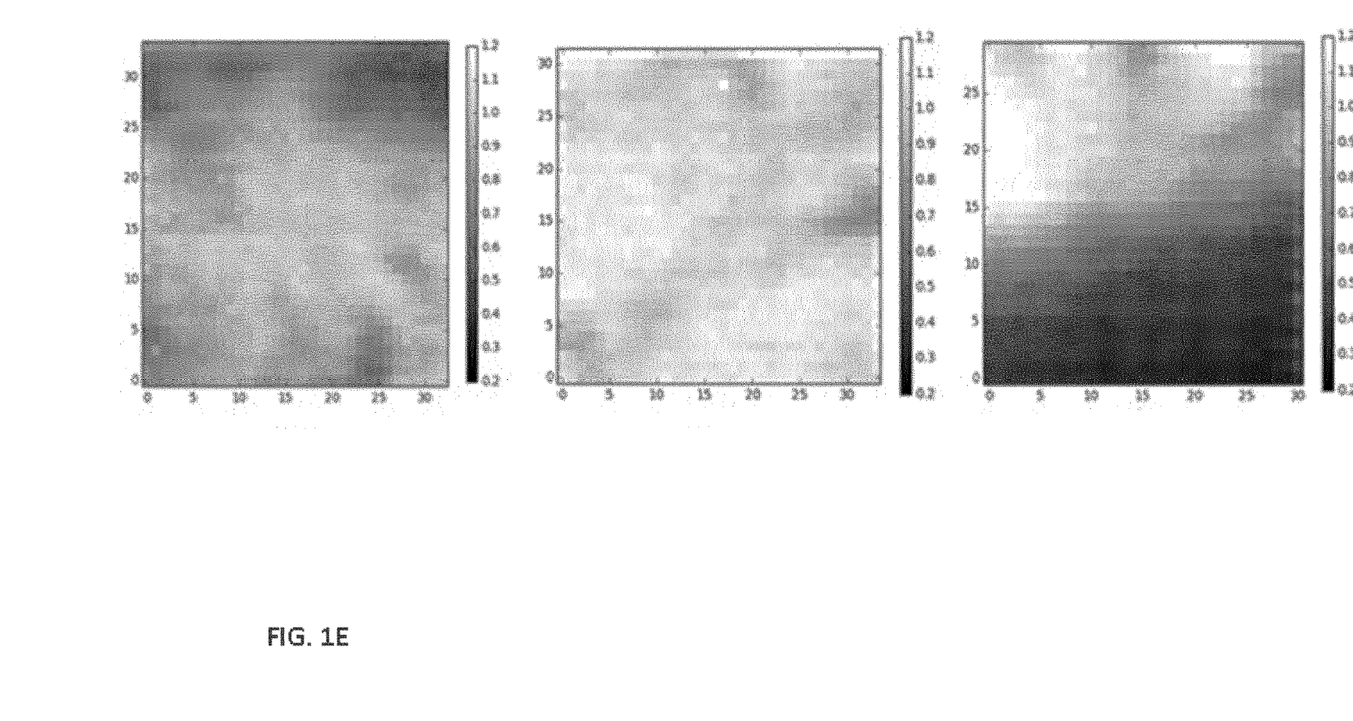
FIG. 1E illustrates example conductivity maps.

As a result, maps of the THz conductivity which represent the quality of the sample 140 may be attained. Some examples of the THz conductivity maps of various thin film material samples are depicted in FIG. 1E. The area of the samples depicted in FIG. 1E is 10 mm×10 mm. The pixel size shown is approximately 250 um. The frequency of the irradiation used was 0.5 THz. The conductivity units are milisiemens (mS). The left graph shows an inhomogeneous sample of a thin film material, as areas with different conductivity can be identified. On the right side, a very-low quality sample of a thin film material is presented. In that sample, two clearly different areas are shown. Finally, the thin film material sample in the center presents a uniform distribution of the conductivity.

Figure 2:
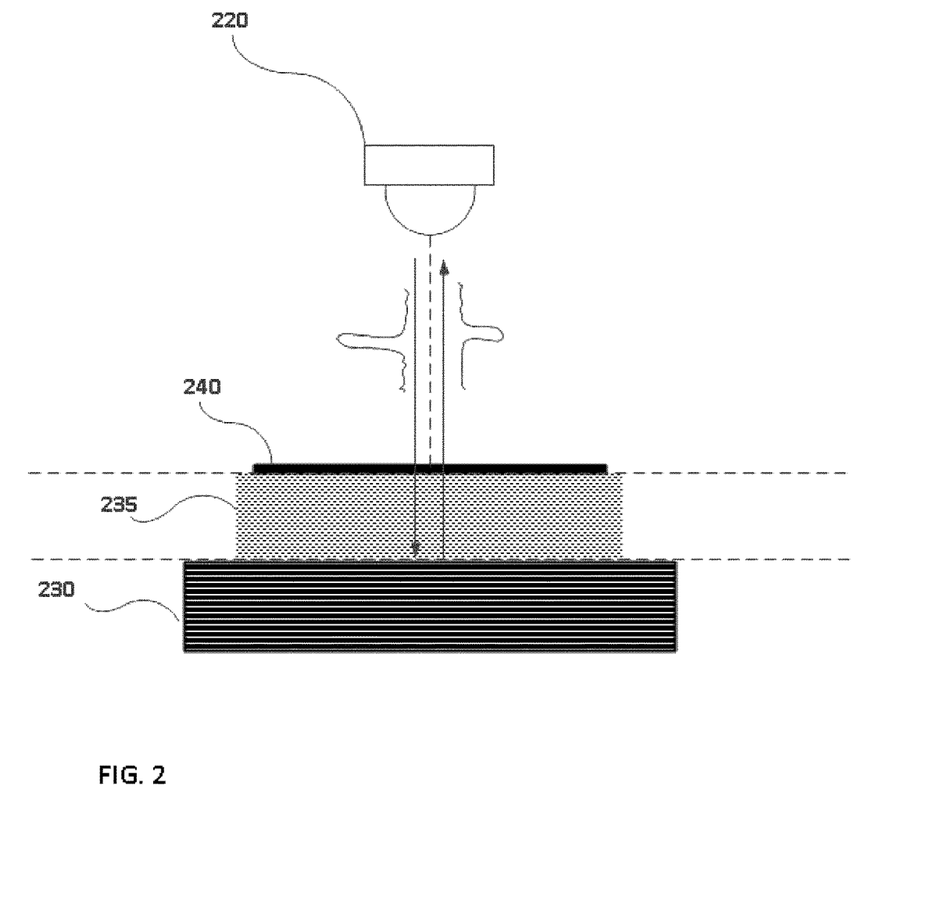
FIG. 2 illustrates an example of a conductivity measurement process.

FIG. 2 illustrates an example of a quality measurement process. A THz module 220 irradiates a thin film 240. The thin film 240 lies on top of a substrate 235. The structure sits on a reflective base 230. The THz module 220 receives the reflection of the irradiation which contains information from the interface between the substrate 235 and the base 230. The device may calculate the parameter indicative of the quality, e.g. conductivity, at a specific irradiated point of the thin film 240 based on said reflection measurement alone or in combination with a similar reflection measurement taken without the thin film. The difference between the two reflection signals will then be a signal attributable only to the thin film material.

Figure 3:
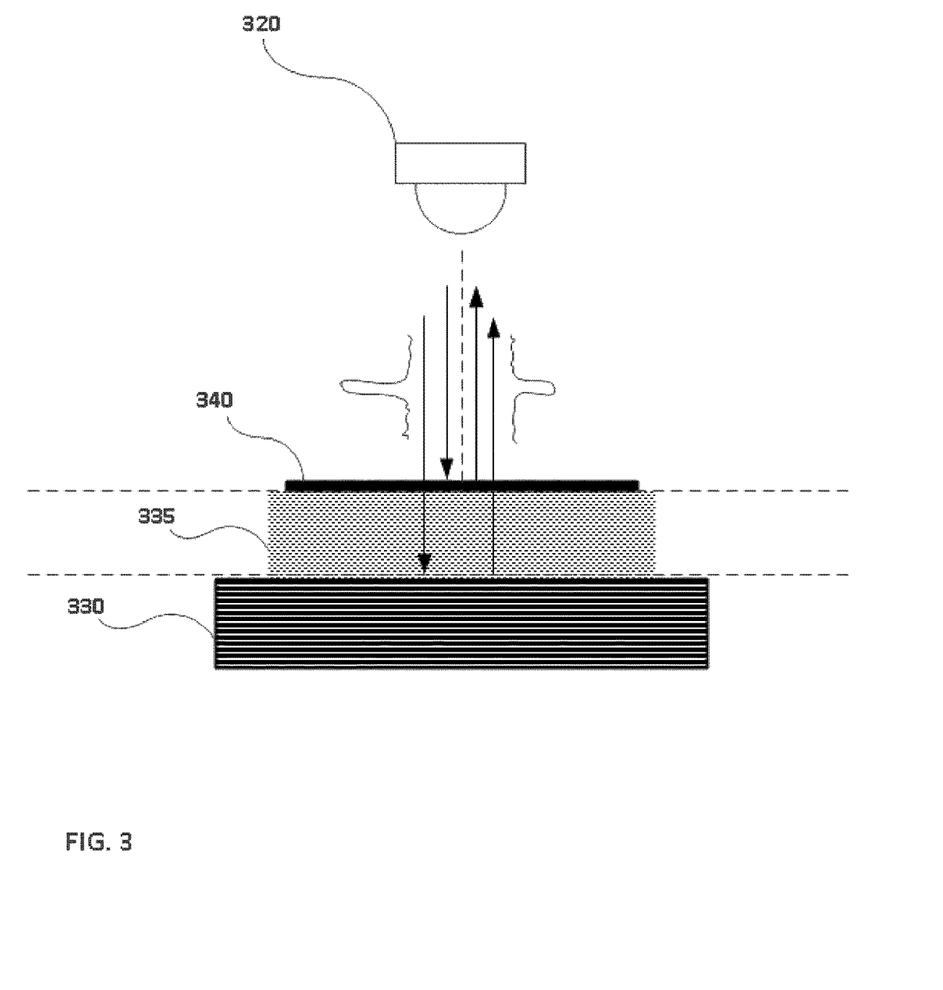
FIG. 3 illustrates another example of a conductivity measurement process.

FIG. 3 illustrates another example of a quality measurement process. A THz module 320 irradiates a thin film 340. The thin film 340 lies on top of a substrate 335. The substrate sits on a reflective base 330. The THz module 320 receives the reflection of the irradiation from the interface between the thin film material 340 and the substrate 335 as well as the reflection which contains information from the interface between the substrate 335 and the reflective base 330. Again, the device may calculate the parameter indicative of the quality, e.g. conductivity, at a specific irradiated point of the thin film 340 based on said two reflection measurements or in combination with similar reflection measurements taken without the thin film. The difference between the corresponding reflection signals will then be signals attributable only to the thin film material.

Figure 4:
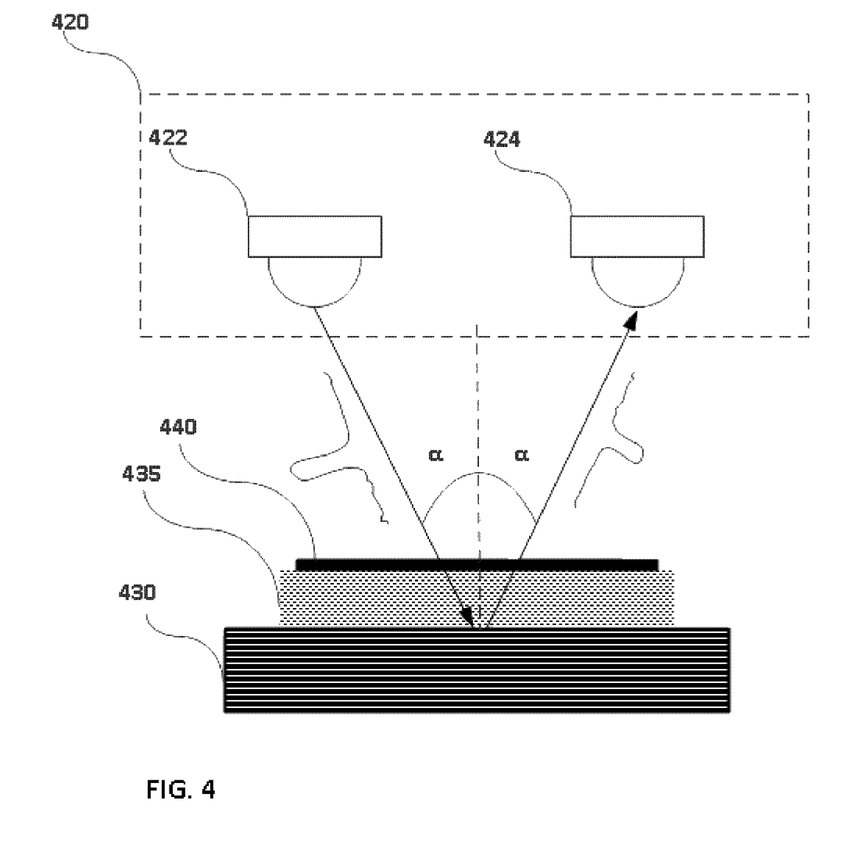
FIG. 4 illustrates another example of a quality measurement process of a thin film sample.

FIG. 4 illustrates yet another example of a quality measurement process. Again, a thin film 440 lies on top of a structure 435. The structure sits on a reflective base 430. In the example of FIG. 4, the irradiation is oblique. It should be noted that the sizes (thicknesses) of the thin film material and of the substrate have been exaggerated for clarity purposes. Taking into account the spot size of the inspection system, the points of entry and exit are substantially the same. That is, a THz module 420 comprises a THz source emitter 422 and a THz detector 424. The THz source 422 irradiates the thin film 440. The THz detector 424 receives a reflection which contains information from the surface of the substrate 435 and another reflection which contains information from the surface of the conductive base 430. A processing module may correct the measurements based on the incident angle of each reflection. For example, each reflection signal may be analyzed in its x and z direction vectors. Then, only the z vectors may be used for determining the relative reflectance of the sample.

Figure 5:
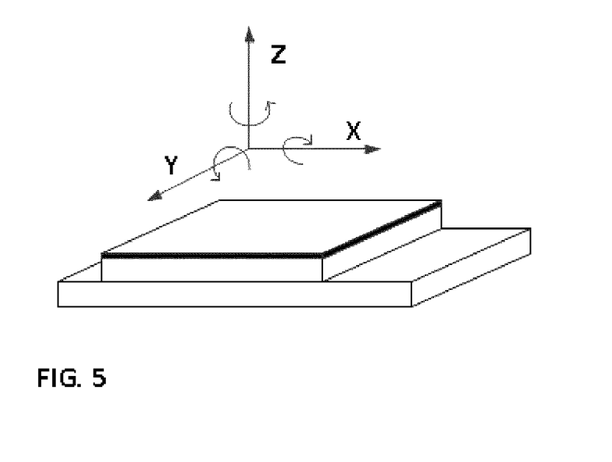
FIG. 5 illustrates the three linear directions (and three rotations).

FIG. 5 illustrates the three linear directions (and three rotations) where the relative movement between the THz module and the thin film may take place. During a measurement process, the z axis movement may be used to enhance the focus of the irradiation, and the x, y axis movement to displace the thin film in order to focus on a different point of the thin film. That way a map may be generated for all points of the thin film material.

Figure 6A:
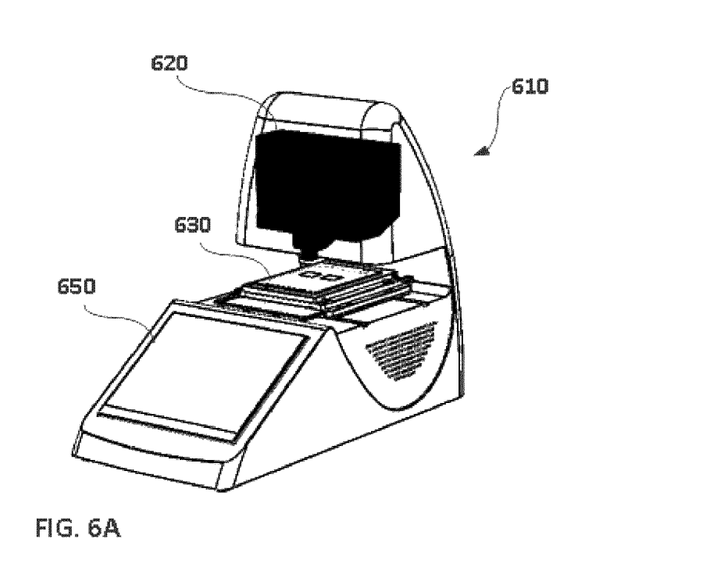
FIG. 6A illustrates an example stand-alone device.
Figure 6B:
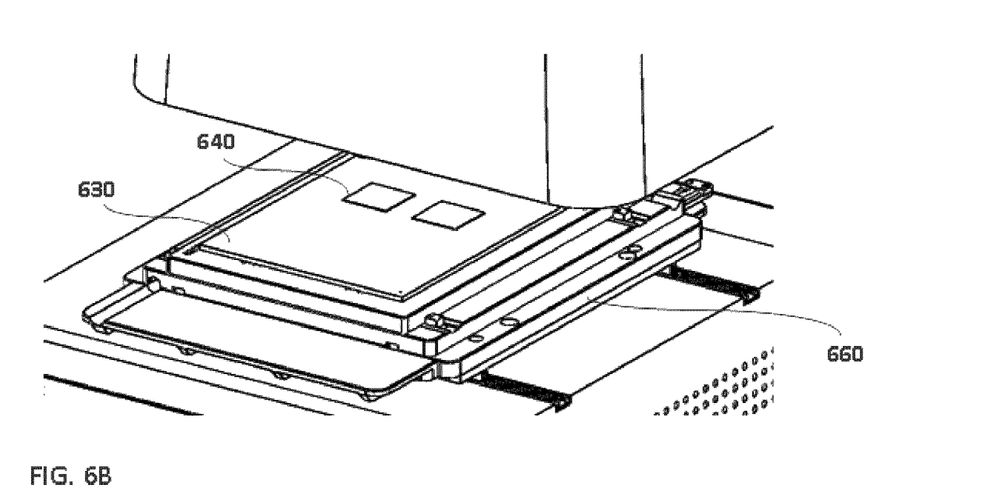
FIG. 6B illustrates a detail of the base of the stand-alone device.

FIG. 6A illustrates an example stand-alone device for making off-line THz inspection of materials. The device 610 comprises a THz module 620, a reflective base 630, on where a thin film structure may be deposited and a control panel 650. FIG. 6B illustrates a detail of the reflective base and an example of actuators in the stand-alone device of FIG. 6A. The reflective base 630 is moveable with respect to the THz module 620. An actuator 660 may displace the base 630 in all three directions. A pair of thin film structures 640 (thin film with substrate) is shown deposited on the reflective base 630.

Figure 7:
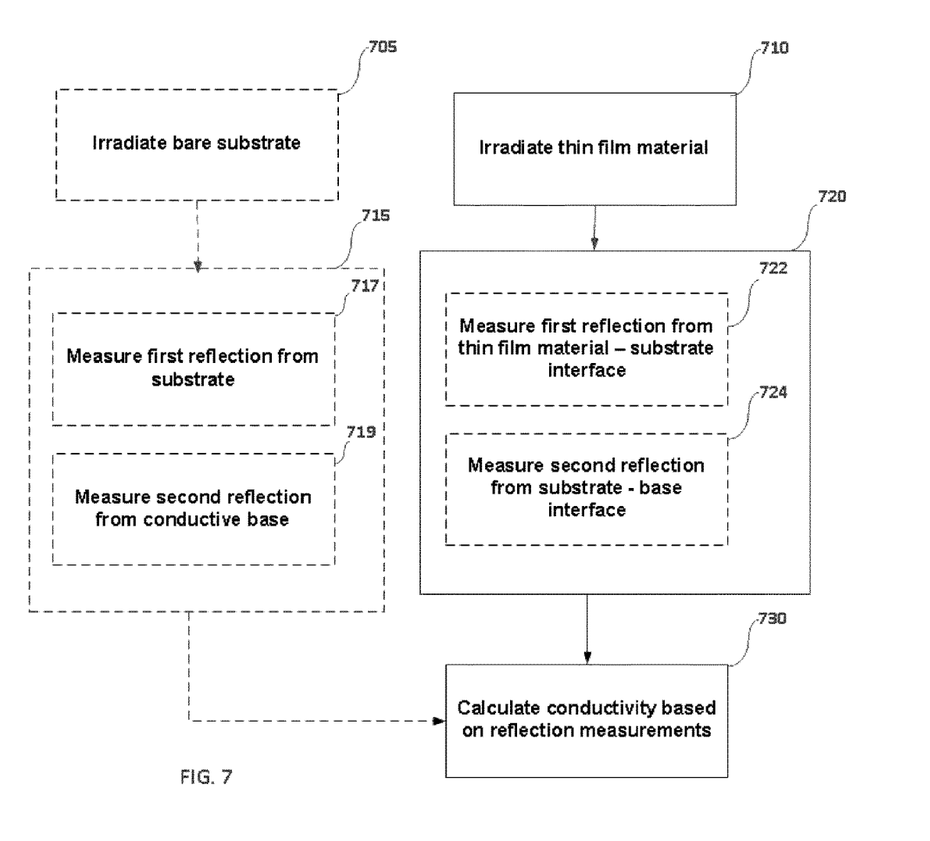
FIG. 7 illustrates a flow diagram of a method of inspecting a thin film material.

FIG. 7 is a flow diagram of a method of inspecting a thin film material according to an example. In a first step 710, a thin film material is irradiated with a THz source emitter. Then, in step 720, at least one reflection of the irradiation which contains information from the thin film material is measured. In step 730, a parameter, e.g. conductivity, indicative of the quality of the thin film material based on said at least one reflection measurement is calculated. The step 720 may comprise a step 722 where a first reflection which contains information from the interface between the thin film material and the substrate is measured. The step 720 may additionally or alternatively comprise step 724 where a second reflection which contains information from the interface between the substrate and the base is measured. Furthermore, the calculation in step 730 may also comprise receiving input from reflection measurements when the thin film is not present. For example, in step 705 the bare substrate may be irradiated. Then in step 715, at least one reflection of the irradiation is measured. Accordingly, the step 715 may comprise a step 717 where a first reflection which contains information from the interface between the air and the substrate is measured. The step 715 may additionally or alternatively comprise step 719 where a second reflection which contains information from the interface between the substrate and the base is measured.

Although only a number of particular embodiments and examples have been disclosed herein, it will be understood by those skilled in the art that other alternative embodiments and/or uses and obvious modifications and equivalents thereof are possible. Furthermore, the disclosure covers all possible combinations of the particular embodiments described. Thus, the scope of the disclosure should not be limited by particular embodiments.

Further, although the examples described with reference to the drawings comprise computing apparatus/systems and processes performed in computing apparatus/systems, the disclosure also extends to computer programs, particularly computer programs on or in a carrier, adapted for putting the system into practice. The program may be in the form of source code, object code, a code intermediate source and object code such as in partially compiled form, or in any other form suitable for use in the implementation of the processes according to the invention. The carrier may be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal, which may be conveyed via electrical or optical cable or by radio or other means. When the program is embodied in a signal that may be conveyed directly by a cable or other device or means, the carrier may be constituted by such cable or other device or means. Alternatively, the carrier may be an integrated circuit in which the program is embedded, the integrated circuit being adapted for performing, or for use in the performance of, the relevant processes.

The invention claimed is:

1. A method to determine the quality of a thin film material by calculating its conductivity, the thin film material provided on a substrate, the thin film material and the substrate forming a thin film material structure, the method comprising:
    placing the thin film material structure on a device, the device comprising a THz source emitter, a THz detector and a reflective base configured to support the thin film material structure,
    the THz source emitter irradiating the thin film material,
    the THz detector measuring a single reflected signal comprising a first reflection from the thin film material and a top surface of the substrate, and a second reflection from a back surface of the substrate after having been passed twice through the thin film material and the substrate, and
    calculating the conductivity of the thin film material as a function of the first and second reflections.

2. The method according to claim 1, further comprising calculating a parameter indicative of a quality of the thin film material as a function of the calculated conductivity.

3. The method according to claim 1, wherein the THz source emitter and the THz detector are integrated in a single THz source/detector module and wherein irradiation and reflection directions overlap.

4. The method according to claim 1, wherein the THz source emitter and the THz detector are separated apart and wherein irradiation is oblique with an angle of incidence $\alpha$.

5. The method according to claim 1, wherein the thin film material comprises an atomically thin material.

6. The method according to claim 1, wherein the thin film material comprises graphene.

7. The method according to claim 1, wherein the thin film material comprises a transition metal dichalcogenide or a transition metal oxide.

8. A method of determining the quality of a thin film material by calculating its conductivity, the thin film material provided on a dielectric substrate forming a thin film material structure, the method comprising:
    providing the thin film material structure on a reflective base;
    irradiating the thin film material structure with a THz source emitter;
    measuring a single reflected signal comprising a first reflection from the thin film material and from a top surface of the dielectric substrate and a second reflection from a bottom surface of the dielectric substrate after having passed twice through the thin film material and the dielectric substrate; and
    calculating the conductivity of the thin film material as a function of the first and second reflections.

9. The method according to claim 8, further comprising measuring the first and second reflections at a plurality of points of the thin film material;
    calculating the conductivity of the thin film material at the plurality of points; and
    generating a conductivity map of the thin film material.

10. The method according to claim 8, further comprising exposing the thin film material structure to one or more external forces, processes, and/or electromagnetic radiation, to modify physical or chemical properties of the thin film material and/or of the substrate, to enhance at least one characteristic of the thin film material and/or of the substrate to facilitate the calculation of the conductivity.

11. The method according to claim 10, wherein the one or more external forces is one or more of an external electric field, voltage source and/or current source and the at least one characteristic is the distribution of positive or negative free charge carriers in selected areas of the thin film structure.

12. A computing device comprising a memory and a processor, wherein the memory stores computer program instructions executable by the processor, the instructions comprising functionality to execute a method of determining the quality of a thin film material by calculating its conductivity according to claim 8.

13. A computer program product comprising instructions to ensure that a computing device implements a method of determining the quality of a thin film material by calculating its conductivity according to claim 8.

14. A method of determining the quality of a thin film material by calculating its conductivity, the thin film material provided on a dielectric substrate forming a thin film material structure, the method comprising:
    providing the thin film material structure on a reflective base;
    irradiating the thin film material structure with a THz source emitter;
    measuring a first signal reflected from the thin film material and from the dielectric substrate;
    measuring a second signal reflected from the reflective base after having passed twice through the thin film and the dielectric substrate; and
    calculating the conductivity of the thin film material as a function of the first and second reflected signals;
    further comprising exposing the thin film material structure to one or more external forces, processes, and/or electromagnetic radiation, to modify physical or chemical properties of the thin film material and/or of the substrate, to enhance at least one characteristic of the thin film material and/or of the substrate to facilitate the calculation of the conductivity; and
    wherein the one or more external forces is an external magnetic field produced by a magnetic fields emitter, on which the thin film material is formed.

* * * * *